(12) United States Patent
Semnani

(10) Patent No.: US 12,728,040 B2
(45) Date of Patent: Sep. 8, 2026

(54) VISION ASSISTANCE APPARATUS AND ASSOCIATED SYSTEMS AND METHODS

(71) Applicant: Rodmehr Tivon Bayegan Semnani, Salt Lake City, UT (US)

(72) Inventor: Rodmehr Tivon Bayegan Semnani, Salt Lake City, UT (US)

( * ) Notice: Subject to any disclaimer, the term of this patent is extended or adjusted under 35 U.S.C. 154(b) by 0 days.

(21) Appl. No.: 18/757,481

(22) Filed: Jun. 27, 2024

(65) Prior Publication Data

US 2025/0000705 A1 Jan. 2, 2025

Related U.S. Application Data

(60) Provisional application No. 63/511,146, filed on Jun. 29, 2023.

(51) Int. Cl.
*A61F 9/08* (2006.01)
*G02B 27/01* (2006.01)
(Continued)

(52) U.S. Cl.
CPC ............ *A61F 9/08* (2013.01); *G02B 27/0172* (2013.01); *G02C 5/001* (2013.01); *G02C 7/088* (2013.01); *G02B 2027/0134* (2013.01); *G02B 2027/0138* (2013.01); *G02B 2027/014* (2013.01); *G02B 2027/0178* (2013.01);
(Continued)

(58) Field of Classification Search
CPC ..... A61F 9/08; G02B 27/017; G02B 27/0172; G02B 2027/0134; G02B 2027/0138; G02B 2027/014; G02B 2027/0178; G02B 2027/0181; G02C 5/001; G02C 7/088; G02C 7/14; G02C 2202/10
See application file for complete search history.

(56) References Cited

U.S. PATENT DOCUMENTS 4,779,972 A 10/1988 Gottlieb
4,958,294 A 9/1990 Hercher et al.
(Continued)

OTHER PUBLICATIONS

PCT International Search Report, PCT/US2024/035928, Oct. 17, 2024 (4 pgs).

(Continued)

*Primary Examiner* — Cory A Almeida
(74) *Attorney, Agent, or Firm* — John P. Davis; Thayne and Davis LLC

(57) ABSTRACT

Embodiments of the disclosed systems and methods provide for a vision assistance apparatus that may enhance the vision of a user and/or provide vision correction. Certain implementations provide for a binocular vision assistance apparatus that may translate an image captured at and/or near a location of a user's impaired eye and translate the image to a location that is perceivable by the user's healthy eye. In certain embodiments, optical systems may be used to translate the image to the location perceivable by the user's healthy eye. In further embodiments, electronic sensors and/or displays may be used. By providing translating certain images to a location perceivable by a user's healthy eye, embodiments disclosed herein may improve the quality of life and functionality of individuals with compromised vision, enabling them to participate more fully in daily activities and/or reducing the limitations imposed by their visual condition(s).

16 Claims, 5 Drawing Sheets

(51) Int. Cl.
*G02C 5/00* (2006.01)
*G02C 7/08* (2006.01)
*G02C 7/14* (2006.01)

(52) U.S. Cl.
CPC ........ *G02B 2027/0181* (2013.01); *G02C 7/14* (2013.01); *G02C 2202/10* (2013.01)

(56) References Cited

U.S. PATENT DOCUMENTS

| | | | | |
|---|---|---|---|---|
| 6,299,304 | B1 | 10/2001 | Demuth | |
| 7,374,284 | B2 | 5/2008 | Peli | |
| 7,789,508 | B2 | 9/2010 | Padula, I et al. | |
| 8,128,221 | B2 | 3/2012 | Grant | |
| 8,696,116 | B2 | 4/2014 | Gottlieb | |
| 11,520,169 | B2 | 12/2022 | Peli et al. | |
| 2004/0179261 | A1 * | 9/2004 | Hara .................. | G02B 27/0172 359/407 |
| 2008/0137033 | A1 | 6/2008 | Padula et al. | |
| 2018/0332219 | A1 * | 11/2018 | Corcoran ............. | H04N 23/635 |
| 2022/0317459 | A1 | 10/2022 | Schuck | |

OTHER PUBLICATIONS

PCT International Written Opinion, PCT/US2024/035928, Oct. 17, 2024 (6 pgs).

Masahiro Toyoura et al., Mono-glass for Providing Distance Information for People Losing Sight in One Eye, Dec. 1, 2012, p. 39, col. 2, paragraph 3; figure 1, (4 pgs).

Field Expansion with Multiplexing Prism Glasses Improves Pedestrian Detection for Acquired Monocular Vision, Jae-Hyun Jung, et al., Jul. 2020, https://tvst.arvojournals.org/article.aspx?articleid=2770504, 7 pgs.

Field Expansion for Acquired Monocular Vision Using a Multiplexing Prism, Jae-Hyun Jung, PhD and Eli Pell, MS, OD, FAAO, Sep. 2018, https://www.ncbi.nlm.nih.gov/pmc/articles/PMC6121741/, 34 pgs.

Vision Aids for People Sighted in One Eye, The N.I.R.E, 2022, https://www.agis.com/SqlFileResource8805.pdf?id=451&resource=pdf, 8 pgs.

Multiplexing prism for field expansion of acquired monocular vision & normal sight, Jae-Hyun Jung and Ell Peli, Mar. 21, 2023, https://scholar.harvard.edu/files/jaehyun_jung/files/jhjung_vision2014_amvns_final.pdf, 1 pg.

AR Goggles Restore Depth Perception To People Blind in One Eye, Nidhi Subbaramanarchive page, Jan. 18, 2013, https://www.technologyreview.com/2013/01/18/253991/ar-goggles-restore-depth-perception-to-people-blind-in-one-eye/, 6 pgs.

Prism Glasses, Mar. 20, 2023, Vision Specialists, https://www.vision-specialists.com/prism-glasses, 7 pgs.

English Language Machine Translation—Health Care Guideline for War Survivors with Unilateral Blindness and Their Health Care Providers. Boroumand et al. Veterans Engineering and Medical Sciences Research Institute. Accessed Mar. 21, 2023, http://www.jmerc.ac.ir/images/textbooks/book_pdf/1389/Mono-Ocular-Veteran.pdf, 103 pgs.

* cited by examiner

VISION ASSISTANCE APPARATUS AND ASSOCIATED SYSTEMS AND METHODS

RELATED APPLICATION

This application claims the benefit of priority under 35 U.S.C. § 119 (e) to U.S. Provisional Patent Application No. 63/511,146, filed Jun. 29, 2023, and entitled "Binocular Vision Assistance Apparatus and Associated Systems and Methods," which is hereby incorporated by reference in its entirety.

COPYRIGHT AUTHORIZATION

Portions of the disclosure of this patent document may contain material which is subject to copyright protection. The copyright owner has no objection to the facsimile reproduction by anyone of the patent document or the patent disclosure, as it appears in the U.S. Patent and Trademark Office patent file or records, but otherwise reserves all copyright rights whatsoever.

SUMMARY OF THE INVENTION

The present disclosure relates generally to systems and methods for assisting with loss of vision, including partial loss of vision. More specifically, but not exclusively, the present disclosure relates to systems and associated methods for managing vision and/or partial vision loss using a vision assistance apparatus.

In a healthy vision system, binocular vision is provided by two eyes working together, providing the brain with two slightly different images of the same scene from different perspectives. These images are then combined by the brain to provide a three-dimensional perception of the world, enabling perception of depth. Depth perception is the ability to perceive the relative distances between objects in three-dimensional space, allowing for the estimation of their size, position, spatial relationships, and the like.

The loss and/or impairment of vision in one eye, which may result in monocular and/or partial monocular vision, often may result in a loss and/or impairment of depth perception by an impacted individual. This may significantly affect the ability of the person to perceive and interact with their surroundings. Specifically, when an individual experiences a loss and/or impairment in the vision of one eye, the binocular differences in perspective that contribute to depth perception with two healthy eyes may be diminished and/or absent. As a result, the brain's ability to triangulate and determine depth from binocular sensory inputs (e.g., binocular disparity, convergence, and/or motion parallax) may be compromised. Without these sensory inputs, the brain may rely on other depth cues such as shading and relative size, which are less precise and can be influenced by various factors, leading to reduced accuracy in an individual's depth perception.

The loss of depth perception may have significant consequences in various aspects of daily life for an individual. For example, activities that require accurate depth perception, such as driving, operating machinery, playing sports, and/or performing other coordinated tasks may become more challenging and/or potentially dangerous for individuals with monocular vision. Similarly, tasks involving hand-eye coordination, depth judgement, and/or spatial awareness may become more difficult to accomplish for an individual with the same level of precision and/or efficiency as they would experience with healthy binocular vision.

Embodiments disclosed herein provide for a system and/or apparatus and/or associated methods that may enhance the depth perception capabilities of an individual that has lost and/or otherwise has impaired binocular vision. Specifically, by providing alternative depth cues using various embodiments of the disclosed systems and/or apparatuses, embodiments disclosed herein may improve the quality of life and functionality of individuals with monocular vision and/or partially monocular vision, enabling them to participate more fully in daily activities and/or reducing the limitations imposed by their visual condition(s).

In various embodiments, a binocular vision assistance apparatus may comprise pair of mirrors and/or prisms which may reflect an image captured from a position and/or point of view of an eye with vision loss and/or impairment onto a mirror and/or prism that may be perceived by another eye not impacted (or less impacted) by vision loss and/or impairment. In further embodiments, one or more cameras and electronic display systems may be used.

Embodiments of the disclosed systems and methods may allow an individual to see an image with their unaffected eye from its own perspective, as well as an image from the perspective of their other eye impacted by vision loss and/or impairment, providing a measure of binocular vision. By using mirrors, prisms, cameras, and/or displays to simulate binocular vision viewable by an individual's unimpacted eye, a measure of depth perception may be restored. The human brain may correct for the single eye seeing the two "images" or points of view similarly to how it may correct for upside down vision as demonstrated in the Erismann and Kohler experiment.

Although various embodiments of the disclosed systems and methods are described in connection with a binocular vision assistance apparatus, it will be appreciated that the disclosed embodiments are not so limited and indeed may be used in connection with correcting, improving, and/or assisting with other vision impairments. For example and without limitation, embodiments disclosed herein may be used to assist with correcting peripheral vision loss (or partial loss) using one or more mirrors, prisms, cameras, and/or displays to simulate improved peripheral vision. Moreover, in further implementations, embodiments disclosed herein may be used to enhance vision, even in individuals without any vision loss. For example and without limitation, embodiments disclosed herein may be used to allow a user to view perspectives outside their traditional field of view (e.g., from behind them and/or extending perpendicularly from the sides of their head).

In various embodiments, a vision assistance apparatus may comprise a frame. The frame may comprise a google frame, a glasses frame, a monocle frame, and/or any other type of frame and/or associated structure that may position various other components of the apparatus is desired positions when worn by a user. In certain embodiments, the frame may comprise a variety of materials including, for example and without limitation, wood, plastic, metal, and/or composite materials and/or combinations thereof. In further embodiments, at least a portion of the frame may be geometrically adjustable to fit a user's face.

In some embodiments, the vision assistance apparatus may be configured to secure to an article of clothing worn by a user. For example and without limitation, the vision assistance apparatus may be configured to secure to and/or otherwise be integrated with a piece of headwear (e.g., a hat and/or the like).

The vision assistance apparatus may further comprise a first optical element coupled to the frame in a first location proximate to a location of an impaired eye of a user when the user is wearing the vision assistance apparatus. The first optical element may be configured to capture an image at the first location from a first perspective. In some embodiments, the first optical element may comprise at least one prism. In further embodiments, the first optical element may comprise a multiple element optical system. The multiple element optical system may comprise one or more mirrors, prisms, lenses, fiber optic lines, waveguides, and/or any other suitable optical element(s) and/or combinations thereof. In certain embodiments, the apparatus may further comprise a first optical element adjustment mechanism configured to adjust at least one of a position and an orientation of at least a portion of the first optical element.

The vision assistance apparatus may further comprise a second optical element coupled to the frame in a second location proximate to a location of a healthy eye of the user when the user is wearing the vision assistance apparatus. The second optical element may be configured to optically translate the image captured by the first optical element at the first location from the first perspective to at least a portion of the second optical element viewable by the user's heathy eye.

In certain embodiments, the second optical element may comprise at least one prism. In further embodiments, the second optical element may comprise a multiple element optical system. The multiple element optical system may comprise one or more mirrors, prisms, lenses, fiber optic lines, waveguides, and/or any other suitable optical element (s) and/or combinations thereof. In certain embodiments, one or more mirrors that may be included in the second optical element (and potentially the first optical element depending on the configuration) may be partially transparent, at least in part. In certain embodiments, the apparatus may further comprise a second optical element adjustment mechanism configured to adjust at least one of a position and an orientation of at least a portion of the second optical element.

In further embodiments, the vision assistance apparatus may further comprise one or more other optical elements. For example, the apparatus may comprise in some implementations a third optical element coupled to the frame in a third location. The second optical element may be configured to capture an image at the third location from a second perspective. The apparatus may further comprise a fourth optical element coupled to the frame in a fourth location proximate to the location of a healthy eye of the user when wearing the vision assistance apparatus, with the fourth optical element being configured to optically translate the image captured by the third optical element at the third location from the third perspective to at least a portion of the fourth optical element viewable by the user's heathy eye. In some embodiments, the second and the fourth optical elements may be integrated into a single compound element providing perspective views translated by the first and third elements.

It will be appreciated that embodiments of the disclosed systems and methods may provide a variety of other benefits in a variety of use cases, and that any improvements, benefits, examples, and/or use cases described herein, including those detailed above, should not be viewed as illustrative and not limiting.

BRIEF DESCRIPTION OF DRAWINGS

The inventive body of work will be readily understood by referring to the following detailed description in conjunction with the accompanying drawings, in which.

DETAILED DESCRIPTION OF THE INVENTION

A description of systems and methods consistent with embodiments of the present disclosure is provided herein. While several embodiments are described, it should be understood that the disclosure is not limited to any one embodiment, but instead encompasses numerous alternatives, modifications, and equivalents. In addition, while numerous specific details are set forth in the following description in order to provide a thorough understanding of the embodiments disclosed herein, some embodiments can be practiced without some or all of these details. Moreover, for the purpose of clarity, certain technical material that is known in the related art has not been described in detail in order to avoid unnecessarily obscuring the disclosure.

The embodiments of the disclosure may be understood by reference to certain drawings. The components of the disclosed embodiments, as generally described and/or illustrated in the figures herein, could be arranged and designed in a wide variety of different configurations. Thus, the following description of the embodiments of the systems and methods of the disclosure is not intended to limit the scope of the disclosure, but is merely representative of possible embodiments of the disclosure. In addition, the steps of any method disclosed herein do not necessarily need to be executed in any specific order, or even sequentially, nor need the steps be executed only once, unless otherwise specified.

Embodiments of the disclosed systems and methods may provide for a binocular vision assistance apparatus that uses using mirrors, prisms, lens, fiber optics, cameras, and/or displays to simulate binocular vision viewable by an individual's healthy eye, restoring a measure of depth perception. Although various examples and use cases described herein may provide for apparatuses and/or associated methods that may be used to correct, improve, and/or otherwise assist with binocular vision, it will be appreciated that embodiments of the disclosure may be used in a variety of other applications, use cases, and/or contexts. For example and without limitation, various embodiments may be used to correct, assist with, and/or improve other types of vision loss including peripheral vision loss. Further embodiments may be used in connection with enhancing vision and/or providing a wearer with different perspective views not otherwise achievable with their natural vision (e.g., providing a user with a greater field of view such as an expanded peripheral view and/or rear view, even if the user does not have a measure of vision loss and/or impairment).

Figure 1:
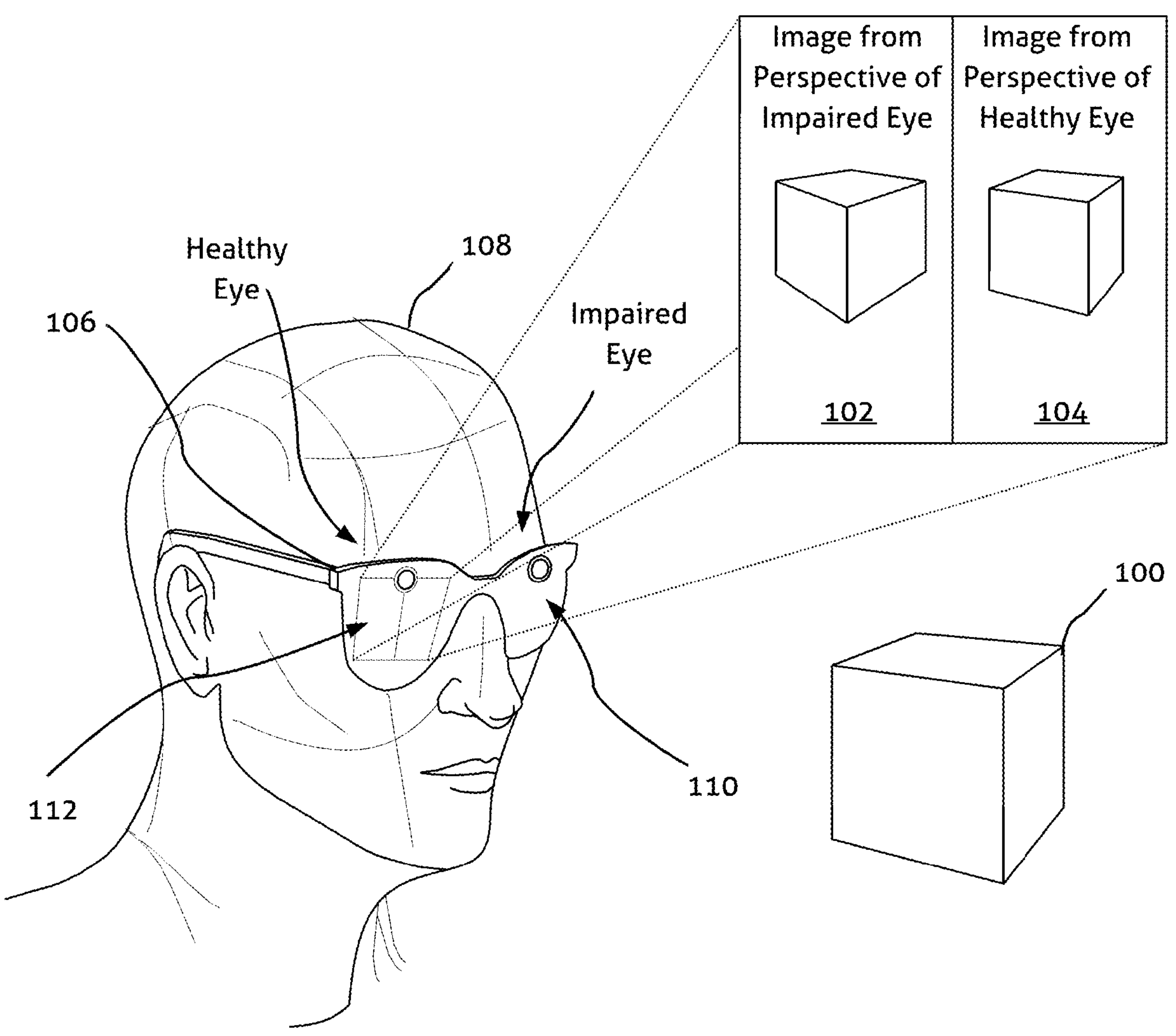
FIG. 1 illustrates a non-limiting example of the use and general functionality of a binocular vision assistance apparatus consistent with certain embodiments disclosed herein.

FIG. 1 illustrates a diagram of a non-limiting example of the use and general functionality of a binocular vision assistance apparatus consistent with certain embodiments disclosed herein. In certain circumstances, a user of a binocular vision assistance apparatus consistent with various disclosed embodiments may have a healthy eye and an impaired eye. Although described herein as a "healthy eye" and an "impaired eye," it will be appreciated that in various contexts and/or use cases a user's healthy eye may not be perfectly healthy and/or functional, but may be considered more functional and/or otherwise less impaired than their "impaired eye." Moreover, although various embodiments and examples described and illustrated herein detail a user's healthy eye as being their right eye and their impaired eye as being their left eye, it will be appreciated that a user's healthy or impaired eye may be located on either the user's left side and/or right side, with various described components of the binocular vision assistance apparatus being configured accordingly.

In some circumstances, an individual's impaired eye may be impaired only partially. For example, an individual may be diagnosed with scotoma due to a blind spot and/or other visual field abnormality in a portion of their vision in one or both eyes but have unimpaired and/or relatively less impaired vision in certain other portions. Embodiments disclosed herein may be used to as correct, assist with, and/or otherwise improve a wearer's vision due to such a partial vision loss in one or both eyes. In further circumstances, an individual may have vision impairment due to reduced ability to move and/or position one and/or both of their eyes. For example, a number of medical conditions may cause ophthalmoplegia, which may result in restricted and/or reduced eye movement. Embodiments disclosed herein disclosed herein may be further used to as correct, assist with, and/or otherwise improve a wearer's vision due to restricted and/or reduced eye movement.

As detailed above and illustrated in FIG. 1, when viewing an object 100 with a healthy vision system, images of the object from two different perspectives 102, 104 (i.e., from the locations of each eye) may be obtained. These slightly different images 102, 104 of the same object 100 from different perspectives may be combined by an individuals' brain to provide a measure of three-dimensional perception of the object 100. With impaired vision, however, the ability to accurately capture one and/or both of these images 102, 104 may be diminished.

Consistent with embodiments disclosed herein, a suitably configured pair of glasses, googles, a single monocle, and/or another wearable device may be used that allows a user to perceive binocular vision through one eye. In various embodiments, a binocular vision assistance apparatus may comprise a frame 106, which may position various elements of the apparatus in desired locations when worn by a user 108. For example and without limitation, various disclosed and illustrated embodiments may use a frame 106 that comprises an eyeglass frame, although other types and/or configurations of frames are also contemplated. Indeed, it will be appreciated any suitable frame structure providing structure for attaching various components of the disclosed apparatus (e.g., first and second elements 110, 112, as described below) and suitably positioning the components relative to a wearer's eyes and/or other positions for operation may be used in connection with the disclosed embodiments.

Like conventional eyeglasses, the frame 106 may comprise one or bridges between lens, which may also include nose pads for resting the frame 106 on wearer's nose bridge. The frame 106 may further comprise one or more temple pieces, which may or may not be hinged, and which may allow the frame 106 to rest on top of a wearer's ears.

The frame 106 may be worn by a user 108 in a variety of ways. For example and without limitation, eyeglass, googles, monocle, and/or similar frames may be supported by a wearer's ear(s) and/or by the bridge of the wearer's nose. The geometry and/or configuration of the frame 106 when worn by the user may position various components in desired locations relative to a user's eyes and/or other positions for suitable operation.

In further embodiments, the frame 106 may be secured and/or otherwise positioned on a wear using other mechanisms including, for example and without limitation, via skin-compatible adhesives, straps, magnetic attachment points (e.g., using complementary magnets adhered to and/or implanted under a wearer's skin), and/or the like. In yet further embodiments, the frame 106 may be coupled and/or otherwise attached to another article worn by the user, positioning the frame 106 in a suitable location for operation. For example and without limitation, the frame 106 may be integrated into and/or otherwise attached to a hat, a helmet, and/or other suitable headwear worn by the user in a manner such that the frame 106 and/or its associated components are suitably positioned for proper operation of the disclosed apparatus.

A variety of materials and/or methods of construction may be used to form the frame 106. The frame 106 may comprise, for example and without limitation, plastic, metal, wood, composites, and/or any other suitable material and/or combination of materials. The frame may be formed using, for example and without limitation, molding (e.g., injection molding), casting, machining (e.g., computerized numerical code ("CNC") machining), 3D printing, and/or any other suitable manufacturing method and/or combination of manufacturing methods. In some embodiments, the frame 106 and/or portions thereof may be adjustable (at least in part), allowing for a more tailored fit and/or configuration to a particular wearers face geometry.

In certain embodiments, the frame 106 may be geometrically and/or dimensionally customized to a particular user, allowing for a more tailored fit of the frame 106 when worn by the user. For example and without limitation, in some embodiments, physical measurements and/or information from 3D scan of a wearer's head may be used to manufacture a frame 106 that is customized to the geometry of a particular wearers face, allowing for improved positioning of components of the apparatus relative to a user's eyes (and/or other desirable relative locations around a user's head).

Consistent with embodiments disclosed herein, the frame 106 may position a first element 110 used to capture an image at a location and/or from a perspective view of an impaired eye and/or other location and/or perspective where corrected, assisted, and/or otherwise improved vision is desired (e.g., peripheral views). As used herein, the term "capture" is to be understood in a manner that may vary depending on the specific implementation of the first element 110. For example, in some embodiments, the first element 110 may optically capture an image from a certain perspective view (e.g., a wearer's impaired eye perspective) and may part of a multiple component optical system to optically translate and/or otherwise reflect the optically captured image to wearer's normal eye. For example and without limitation, the first element 110 may comprise one or more prisms, lenses, mirrors, fiber optics and/or optical waveguides that, potentially in conjunction with other components in an optical system, may optically translate an image captured from a first location/perspective, such as a location/perspective of a wearer's impaired eye, to a second location/perspective, such as a location/perspective of a wearer's healthy eye.

In further embodiments, the first element 110 may comprise one or more sensors used to electronically capture an image, as shown in FIG. 1. For example, the first element 110 may comprise one or more cameras and/or other similar sensor systems that, in conjunction with display elements, may electronically translate an image captured from a first location/perspective to a display that may be viewable and/or perceivable by a user in a second location (e.g., a location of their healthy eye). Although the described embodiments detail a camera and/or other sensor system capturing an image, it will be appreciated that such an image capture may be part of a video feed provided to the display (that is, the image may not necessarily comprise a single captured image, but may comprise multiple images as part of a video feed from the camera and/or other sensor system to the display).

The frame may further position a second element 112 used to provide the user with the image captured by the first element 110 in a location perceivable by their healthy eye. For example, in some embodiments, the image captured by the first element 110 may be translated to a second element 112 positioned in front of the user's healthy eye.

A variety of types and/or configurations of second elements 112 may be used in connection with the disclosed embodiments. For example and without limitation, in some embodiments, the second element 112 may comprise a mirror, which may be fully and/or partially reflective, and/or a prism which may direct a reflected image from the first element 110 towards the user's healthy eye. In a further non-limiting example, the second element 112 may comprise an electronic display, which in certain implementations may comprise a partially transparent electronic display, configured to display an image captured by a camera system of the first element. 110 In some embodiments, various suitable combinations of prisms, mirrors, waveguides, fiber optics, and/or other optical elements (e.g., lenses) may be used to form the first and/or second elements 110, 112 and or optical systems optically coupling the elements 110, 112.

Figure 2:
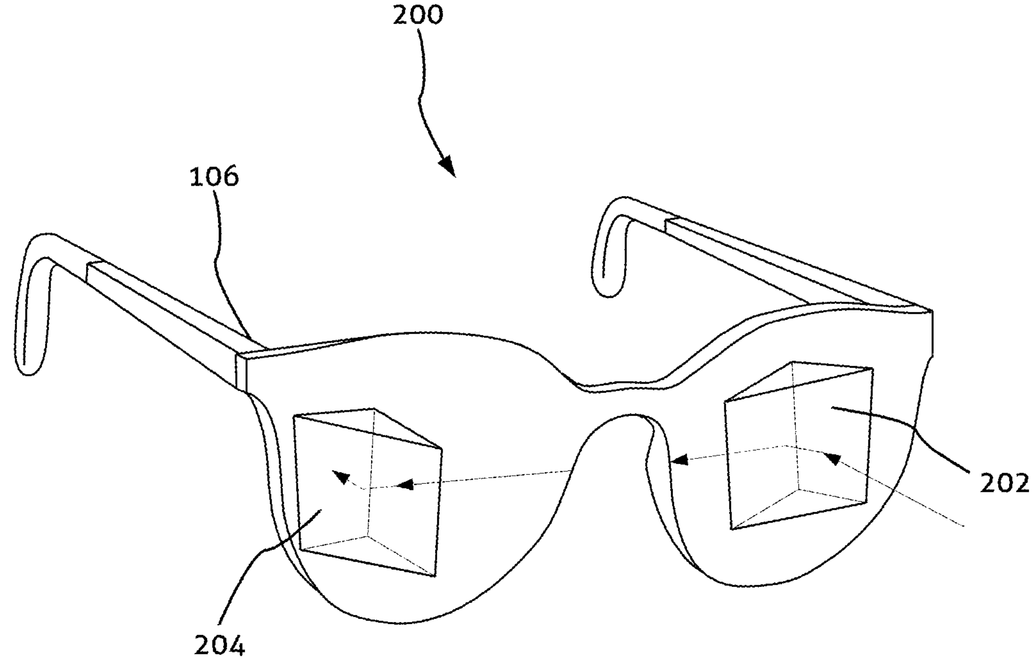
FIG. 2 illustrates a non-limiting example of a binocular vision assistance apparatus that comprises an optical prism system consistent with certain embodiments disclosed herein.

FIG. 2 illustrates a non-limiting example of a binocular vision assistance apparatus 200 that comprises a prism system consistent with certain embodiments disclosed herein. The illustrated apparatus comprises a pair of prism elements 202, 204 secured in position by a frame 106. As shown, the prism elements 202, 204 of the illustrated non-limiting example are configured to reflect an image captured by a first prism element 202 at a location of wearer's impaired eye to a second prism element 204 which may reflect the image so that the image is perceivable and/or otherwise viewable by the wearer's healthy eye. By reflecting the image captured at a location of the user's impaired eye by the first prism element 202 to the second prism element 204 which may reflect the image such that it is perceivable and/or otherwise viewable the user's healthy eye, the user may be provided with a measure of binocular vision.

In certain embodiments, the apparatus 200 may be configured such that the user may simultaneously perceive both the image captured and reflected by the prism elements 202, 204—that is, the image captured at and/or near the position of the user's impaired eye—as well as the image captured by the user's healthy eye. For example, the second prism element 204 may be positioned to occupy only a portion of a field of view of the user's healthy eye, with the user's healthy eye being able to perceive objects normally through the other portion of the field of view (e.g., through an aperture defined by the frame 106, potentially through a lens secured in the frame 106). This may permit the user to view an object from two different perspectives through a single healthy eye, providing a measure of binocular vision and allowing the user's brain to translate the two images to allow for improved perception of depth. For example, in some implementations, a user's optical vision system may allow for signals from one eye to be sent to both left and right sides of the brain (e.g., via the optic chiasm), which may be interpreted by the brain into a field of view providing a measure of depth perception.

Although FIG. 2 illustrates the use of optical prism elements 202, 204, it will be appreciated that in further embodiments may comprise one or more mirrors, which may be fully and/or partially reflective. In yet further embodiments, suitable combinations of mirrors, prisms, waveguides, fiber optics, and/or other optical devices may be used. For example, it will be appreciated that more complex and/or compound optical systems having multiple optical components may be used to capture an image at a first location/perspective (e.g., a location/perspective of an impaired eye) and optically translate the image to another location perceivable by a user. In yet further embodiments, one or more optical vision correction elements (e.g., prescription corrective lenses and/or the like) may be included in the optical system consistent with various aspects of the disclosed embodiments, allowing for improved function with user's that may require a measure of vision correction.

The optical system comprising the prism elements 202, 204 (and indeed any other optical devices, elements, and/or components used in connection with the disclosed embodiments) may be mounted and/or otherwise coupled to the frame 106 in a variety of suitable ways. For example and without limitation, in some embodiments, the prism elements 202, 204 and/or other optical components may be mechanically coupled to the frame 106 in suitable positions (e.g., via screws and/or other mechanical securement mechanisms, via compression fit mechanisms, etc.). In further embodiments, the prism elements 202, 204 and/or other optical components may be coupled to the frame 106 in suitable positions using adhesives. In yet further embodiments, the prism elements 202, 204 and/or other optical components and/or portions thereof may be integrally formed in the frame 106. For example and without limitation, in some implementations, the prism elements 202, 204 and/or other optical components and/or portions thereof may be formed as part of a manufacturing process of the frame 106.

In certain embodiments, the prism elements 202, 204 and/or other optical components may be permanently coupled and/or mounted to the frame 106. In further embodiments, the prism elements 202, 204 and/or other optical components (and/or subsets thereof) may be selectively removable, which may allow the apparatus 200 to function as a normal piece of eyewear. In further embodiments, one or more adjustment structures and/or mechanisms (e.g., adjustable gimbles, translation stages, and/or the like) may be integrated into the frame 106 and/or the prism elements 202, 204 (and/or other optical components) that may allow the prism elements 202, 204, and/or other optical components to be adjustable in position and/or orientation, allowing for more precise tuning and/or adjustment of these components when worn by a user to improve operability (potentially in addition to and/or in lieu of adjustability provided by the structure of the frame 106 itself).

Figure 3:
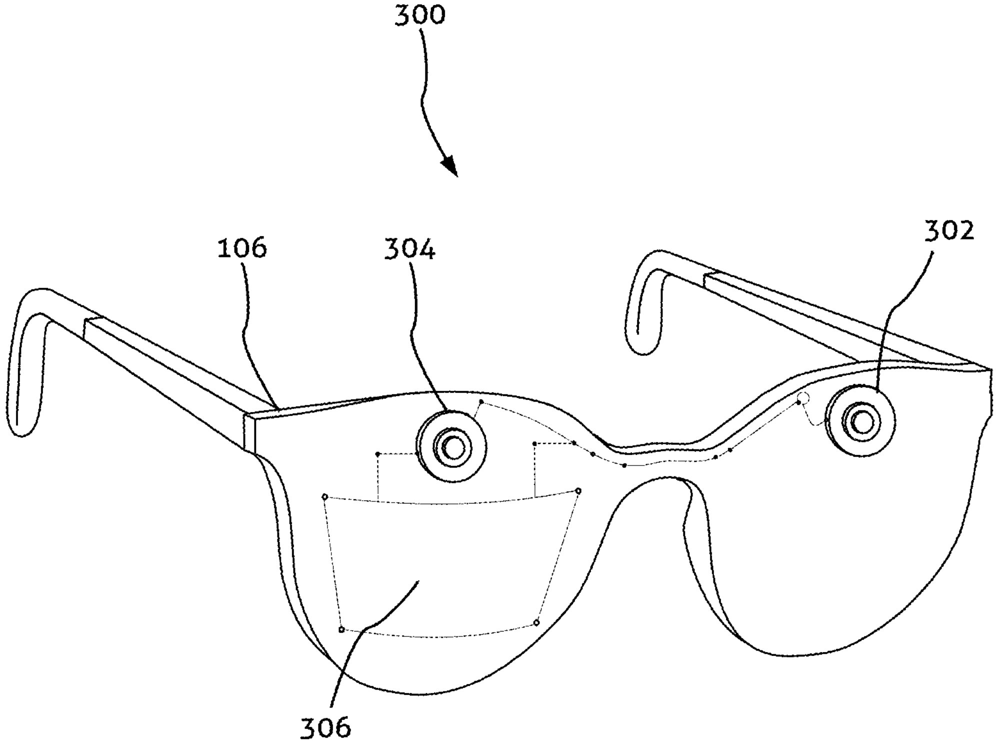
FIG. 3 illustrates a non-limiting example of a binocular vision assistance apparatus that comprises a camera and display system consistent with certain embodiments disclosed herein.

FIG. 3 illustrates a diagram of a binocular vision assistance apparatus 300 that comprises a camera 302 and display system 306 consistent with embodiments disclosed herein. The illustrated apparatus comprises an electronic camera 302 and an electronic display system 306 secured in associated positions relative to a user by the frame 106. As shown, a first camera system 302 may be positioned by the frame 106 at and/or near a location of a user's impaired eye when worn by the user. The electronic display 306 may be positioned by the frame 106 in a location that may be viewable by a user's healthy eye when worn by the user.

Consistent with embodiments disclosed herein, the first camera system 302 may be configured to capture an image which may be displayed on the electronic display 306. The user may be able to perceive the image displayed on the electronic display 306 using their healthy eye as well as an image from the perspective of their healthy eye (which may be viewable through an aperture and/or opening defined by the frame 106 and/or via display 306 and/or another display based on being captured by another camera system 304, as detailed below). This may allow the user to view images from the perspective of both their healthy eye and captured by the first camera system 302 at a position of their impaired eye providing them with a measure of binocular vision and/or depth perception cues. By permitting the user to view an object from two different perspectives through a single healthy eye, a measure of binocular vision may be provided, allowing the user's brain to translate the two images to allow for improved perception of depth.

In some embodiments, a binocular vision assistance apparatus 300 consistent with certain embodiments disclosed herein may comprise a single camera system 302 capturing an image from or proximate to a location of a user's impaired eye for display on the electronic display 306. An image from the user's healthy eye may be captured naturally by their healthy eye (potentially through a lens, which may comprise a corrective lens and/or device which may be integrated into the frame 106 and/or secured by the frame 106 and/or be a separate vision correction system as may be the case with a contact lens and/or a separate corrective lens).

A variety of types and/or configurations of display(s) 306 may be used in connection with the disclosed embodiments. For example and without limitation, in some embodiments, the display(s) 306 may be located proximate and/or adjacent to a portion of an aperture and/or opening defined by the frame 106 and be positioned such that a user may review the display(s) 306 with their healthy eye while simultaneously viewing an object and/or surroundings through the frame aperture. In some embodiments, the electronic display 306 and/or a portion thereof may comprise a partially transparent electronic display.

Although a single display 306 is illustrated in connection with FIG. 3, it will be appreciated that in further embodiments, multiple displays may be employed in various suitable locations/positions to be viewable by a user. Indeed, as discussed in more detail below, in embodiments where multiple cameras may be employed, multiple displays may be used. In further embodiments, a single display may be used to display images captured by multiple cameras (e.g., with different images displayed on different portions of the display).

In some implementations, a vision assistance apparatus 300 may comprise multiple camera systems 302, 304 capturing an image from multiple locations and/or perspectives. For example, as illustrated, the binocular vision assistance apparatus 300 may comprise two camera systems: a first camera system 302 capturing an image from or proximate to a location of a user's impaired eye and a second camera system 304 capturing an image from or proximate to a location of a user's healthy eye. The two images may be viewed by a user's healthy eye via the electronic display 306 (and/or multiple displays) coupled to the camera systems 302, 304. As discussed above, in various embodiments, one or more of the electronic display(s) 306 may be partially transparent.

The one or more cameras 300, 304 and/or display(s) 306 (and indeed any other optical devices, elements, and/or components used in connection with the disclosed embodiments) may be mounted and/or otherwise coupled to the frame 106 in a variety of suitable ways. For example and without limitation, in some embodiments, the one or more cameras 300, 304 and/or display(s) 306 may be mechanically coupled to the frame 106 in suitable positions (e.g., via screws and/or other mechanical securement mechanisms, via compression fit mechanisms, etc.). In further embodiments, the one or more cameras 300, 304 and/or display(s) 306 may be coupled to the frame 106 in suitable positions using adhesives.

In certain embodiments, the one or more cameras 300, 304 and/or display(s) 306 may be permanently coupled and/or mounted to the frame 106. In further embodiments, the one or more cameras 300, 304 and/or display(s) 306 (and/or subsets thereof) may be selectively removable, which in some implementations may allow the apparatus 300 to function as a normal piece of eyewear. In further embodiments, one or more structures and/or mechanisms (e.g., adjustable gimbles, translation stages, and/or the like) may be integrated into the frame 106 and/or the one or more cameras 300, 304 and/or display(s) 306 that may allow the one or more cameras 300, 304 and/or display(s) 306 to be adjustable in position and/or orientation, allowing for more precise tuning and/or adjustment of these components when worn by a user to improve operability (potentially in addition to and/or in lieu of adjustability provided by the structure of the frame 106).

In various embodiments, as discussed in more detail below in reference to FIG. 5, the operation of the one or more cameras 300, 304 and/or display(s) may be controlled by a suitable microcontroller and/or other control system. The control system may be integral to one or more of the camera 300, 304, and/or displays 306 and/or may be separately implemented and coupled to the frame 106 in a suitable location. Among other things, the control system may communicatively couple and control the operation of the various electronic elements of the disclosed apparatus.

Figure 4:
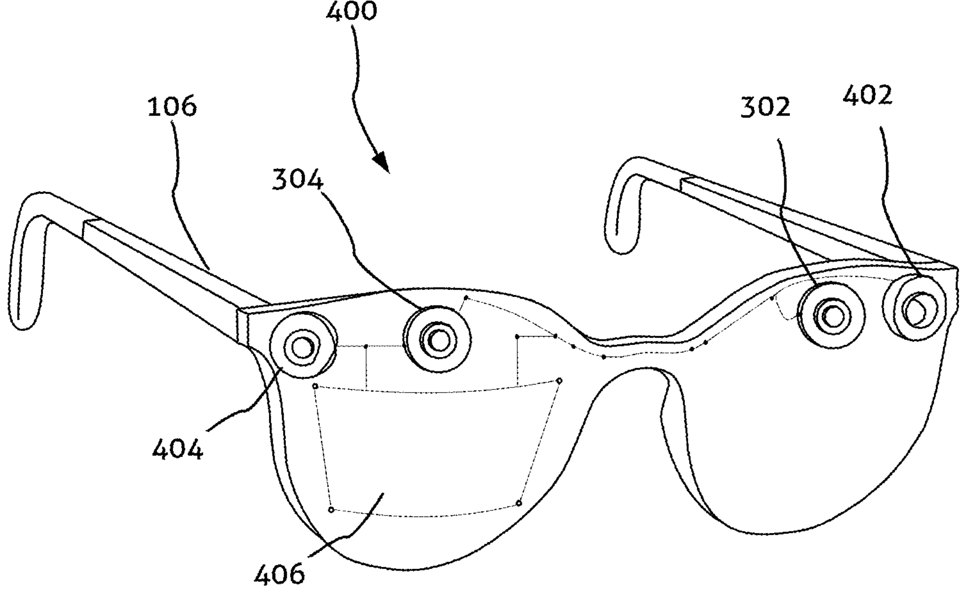
FIG. 4 illustrates a non-limiting example of a vision assistance apparatus providing multiple perspective views consistent with certain embodiments disclosed herein.

FIG. 4 illustrates a non-limiting example of a vision assistance apparatus 400 providing multiple perspective views consistent with certain embodiments disclosed herein. As discussed above, various embodiments of the disclosure may be used to correct, assist with, and/or improve other types of vision loss including peripheral vision loss. Further embodiments may be used in connection with enhancing vision and/or providing a wearer with different perspective views not otherwise achievable with their natural vision (e.g., providing a user with a greater field of view such as an expanded peripheral view and/or rear view, even if the user does not have a measure of vision loss and/or impairment).

Consistent with certain embodiments disclosed herein, a vision assistance apparatus 400 may comprise multiple camera systems 302, 304, 402, 404 capturing images from multiple locations and/or perspectives. For example, camera systems 302, 304 may be used to capture images in a forward orientation relative to a user and/or the frame 106, which may correspond (and/or be similar) to the perspective views of a user with normal vision looking forward. Additional camera systems 402, 404 may be used to capture images that correspond to a user's peripheral vision. For example, camera system 402 may be used to capture an image of a user's left peripheral vision and camera 404 may be used to capture an image of a user's right peripheral vision. The images captured by one or more of these peripheral camera systems 402, 404 may be provided to the display 406, which may be viewable and/or otherwise perceivable by the user.

In various embodiments, a single display 406 may be used to display images from the multiple camera systems 302, 304, 402, 404. In some embodiments, via a user interface associated with the apparatus 400, a user may be able to selectively display which captured camera view(s) of the multiple camera systems 302, 304, 402, 404 are displayed (e.g., by toggling between displayed camera views using a suitably configured interface of the apparatus 400, displaying multiple camera views simultaneously in groups that may be selectable by the user, etc.). In further embodiments, multiple displays may be employed where, in some implementations, each display may be configured to display images captured by an associated camera system of the multiple camera systems (or a plurality of the cameras of camera systems 302, 304, 402, 404). As discussed above, in various embodiments, one or more of the electronic display (s) 406 and/or portions thereof may be partially transparent, allowing a user to simultaneously view an image on the display as well as perceive their surroundings through the display 406.

Although the illustrated vision assistance apparatus 400 providing multiple perspective views is shown as being implemented using cameras systems 302, 304, 402, 404 and/or other sensors and one or more electronic displays 406, it will be appreciated that a multiple perspective view apparatus 400 may be further implemented using suitable optical systems, including multiple element optical systems. For example, may be used in optical systems that optically translate an images captured from multiple locations/perspectives (e.g., a wearers peripheral vision perspective, behind their head, a location/perspective of a compromised eye, etc.) to a location/perspective of a wearer's healthy eye. In further embodiments, optical systems may interface with various aspects of the disclosed electronic systems (e.g., electronic sensors and/or displays) to achieve various device functionality detailed herein.

Figure 5:
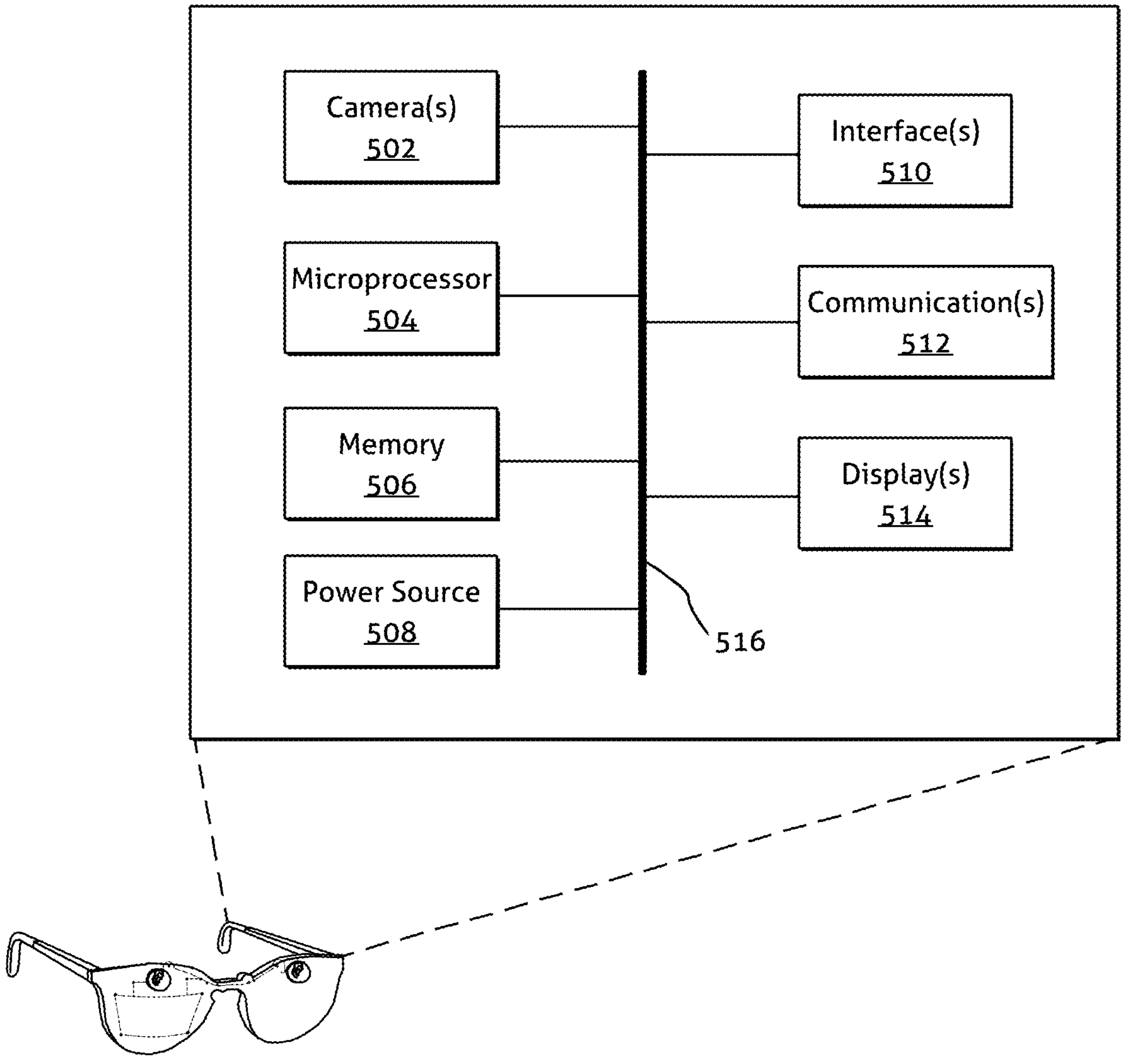
FIG. 5 illustrates a non-limiting example of a vision assistance apparatus electronic control system consistent with embodiments certain embodiments disclosed herein.

FIG. 5 illustrates a non-limiting example of a vision assistance apparatus electronic control system 500 consistent with embodiments certain embodiments disclosed herein. In various embodiments, the operation of the one or more cameras 502 and/or displays 514 may be controlled by a suitable microcontroller and/or other control system. In various embodiments, the control system and/or its various elements may be integral to one or more of the camera systems and/or displays and/or may be separately implemented and coupled to the frame 106 in a suitable location.

The control system may comprise for example and without limitation, one or more microprocessors 504 and/or other processor units, memory 506 and/or other electronic storage, one or more interfaces 510, which may comprise physical and/or electronic interfaces, that may allow for users to interact with the apparatus (e.g., toggling between viewed images, adjusting settings, turning the apparatus on/off, adjusting display transparency, and/or the like), one or more communication interfaces(s) 512 allowing the apparatus and/or associated control systems to communication with other systems and/or services (e.g., to receive software updates, etc.), and/or the like. A power source 508 (e.g., a battery power source) may be further provided to power various elements on the disclosed apparatus 502-506, 510-514. In certain embodiments, a bus 516 may be used to couple (e.g., communicatively couple and/or potentially power) the various illustrated elements 502-514.

The operation of the apparatus may be generally controlled by the microprocessor 504 and/or other processor units by executing software instructions and programs stored in the memory 506 (and/or other computer-readable media, such as memory, which may be removable). The memory 506 may store a variety of executable programs or modules for controlling the operation of the system. For example, the memory 506 may include an operating system ("OS") that may manage and coordinate, at least in part, and/or system hardware resources and provide for common services for execution of various applications.

The memory 506 may further include, without limitation, communication software configured to enable in part communication with and by the system, one or more applications, imaging processing software, camera and/or display drivers, and/or any other information, modules, and/or applications configured to implement embodiments of the systems and methods disclosed herein.

The various embodiments disclosed herein are not inherently related to any particular processing and/or control system, and may be implemented by a suitable combination of hardware, software, and/or firmware. Software implementations may include one or more computer programs comprising executable code/instructions that, when executed by a processor, may cause the processor to perform a method defined at least in part by the executable instructions. The computer program can be written in any form of programming language, including compiled or interpreted languages, and can be deployed in any form, including as a standalone program or as a module, component, subroutine, or other unit suitable for use in a computing environment.

Although the foregoing has been described in some detail for purposes of clarity, it will be apparent that certain changes and modifications may be made without departing from the principles thereof. It should be noted that there are many alternative ways of implementing both the systems and methods described herein. Accordingly, the present embodiments are to be considered as illustrative and not restrictive, and the invention is not to be limited to the details given herein but may be modified with the scope and equivalents of the described embodiments and the appended claims.

The invention claimed is:

1. A vision assistance apparatus comprising:

a frame;

a first optical element coupled to the frame in a first location proximate to a location of an impaired eye of a user when wearing the vision assistance apparatus, the first optical element being configured to capture an image at the first location from a first perspective;

a second optical element coupled to the frame in a second location proximate to a location of a healthy eye of the user when wearing the vision assistance apparatus, the second optical element being configured to optically translate the image captured by the first optical element at the first location from the first perspective to a first portion of the second optical element viewable in a first portion of the user's vision from their healthy eye, the second optical element being further configured to provide an image captured from the perspective of a user's healthy eye on a second portion of the second optical element, the second portion of the second optical element being laterally adjacent to the first portion of the second optical element, the second portion being viewable in a second portion of the user's vision from their healthy eye, such that the first portion of the second optical element and the second portion of the second optical element are simultaneously viewable by the user's healthy eye.

2. The vision assistance apparatus of claim 1, wherein the first optical element comprises at least one prism.

3. The vision assistance apparatus of claim 1, wherein the second optical element comprises at least one prism.

4. The vision assistance apparatus of claim 1, wherein at least one of the first optical element and the second optical element comprises a multiple element optical system.

5. The vision assistance apparatus of claim 4, wherein the multiple element optical system comprises one or more lenses, fiber optic lines, mirrors, and waveguides.

6. The vision assistance apparatus of claim 1, wherein the second optical element comprises at least one mirror.

7. The vision assistance apparatus of claim 6, wherein the at least one mirror comprises a partially transparent mirror.

8. The vision assistance apparatus of claim 1, wherein the frame comprises one or more of a plastic material, a wood material, a metal material, and a composite material.

9. The vision assistance apparatus of claim 1, wherein at least a portion of the frame is geometrically adjustable to fit the user's face.

10. The vision assistance apparatus of claim 1, wherein the apparatus further comprises a first optical element adjustment mechanism, the first optical element adjustment mechanism being configured to adjust at least one of a position and an orientation of at least a portion of the first optical element.

11. The vision assistance apparatus of claim 1, wherein the apparatus further comprises a second optical element adjustment mechanism, the second optical element adjustment mechanism being configured to adjust at least one of a position and an orientation of at least a portion of the second optical element.

12. The vision assistance apparatus of claim 1, wherein the vision assistance apparatus is configured to secure to a clothing article worn by the user.

13. The vision assistance apparatus of claim 12, wherein the clothing article comprises a headwear article.

14. The vision assistance apparatus of claim 1, wherein the apparatus further comprises:

a third optical element coupled to the frame in a third location, the third optical element being configured to capture an image at the third location from a third perspective.

15. The vision assistance apparatus of claim 14, wherein the apparatus further comprises:

a fourth optical element coupled to the frame in a fourth location proximate to the location of a healthy eye of the user when wearing the vision assistance apparatus, the fourth optical element being configured to optically translate the image captured by the third optical element at the third location from the third perspective to at least a portion of the fourth optical element viewable by the user's healthy eye.

16. The vision assistance apparatus of claim 1, wherein the frame comprises one or more of a goggle frame, a glasses frame, and a monocle frame.

* * * * *